Figure 1:
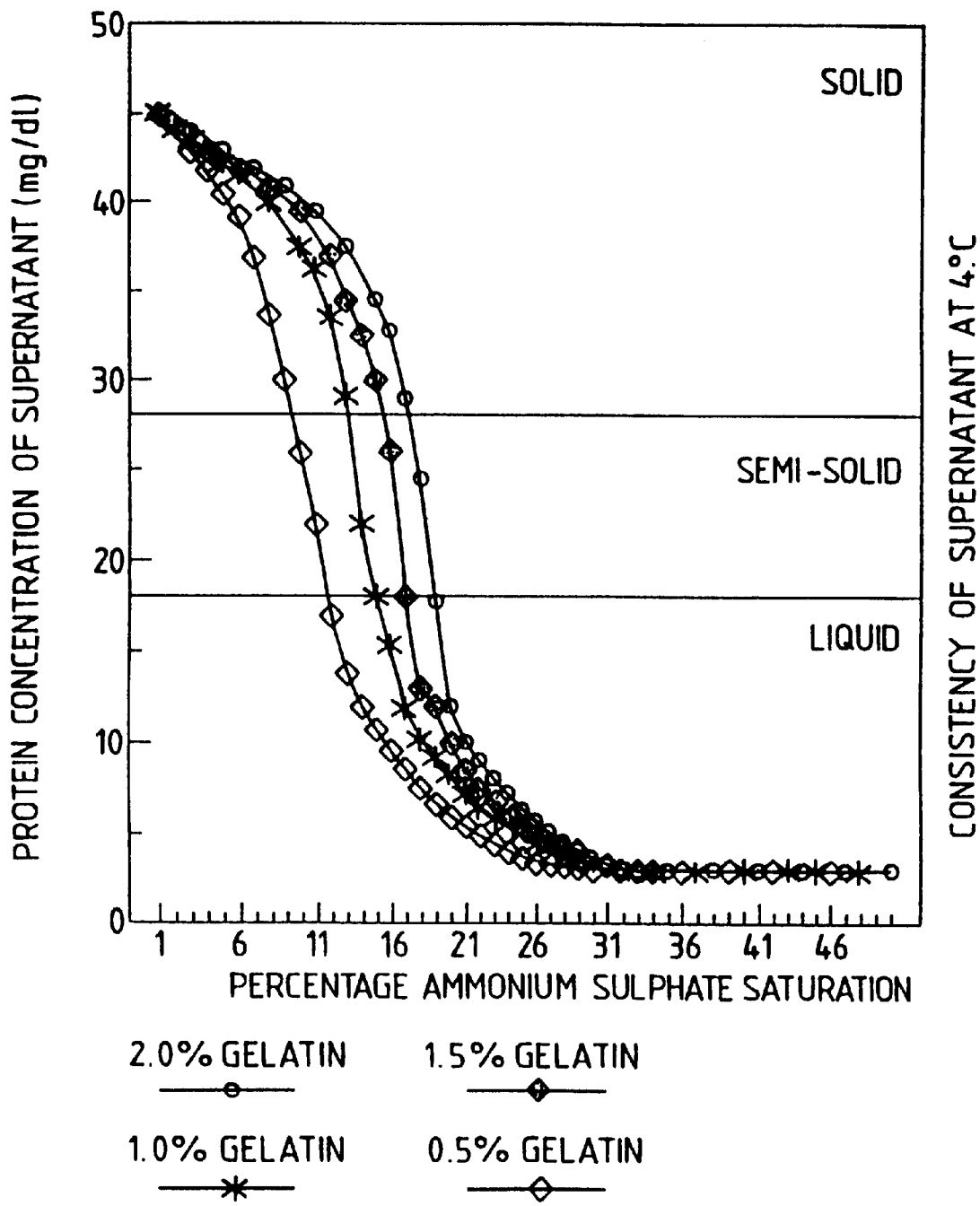

United States Patent [19]

Ansfield

[11] Patent Number: 5,910,446
[45] Date of Patent: Jun. 8, 1999

[54] DETECTION OF HEAT STABLE PROTEINS FROM MEAT OF RUMINANT

[75] Inventor: Michael Ansfield, Stratford-upon-Avon, United Kingdom

[73] Assignee: The Secretary of State for the Minister of Agriculture Fisheries & Food in Her Britannic Majesty's Government of the United Kingdom of Great Britain and Northern Ireland, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/596,189

[22] PCT Filed: Aug. 4, 1994

[86] PCT No.: PCT/GB94/01715

§ 371 Date: Feb. 15, 1996

§ 102(e) Date: Feb. 15, 1996

[87] PCT Pub. No.: WO95/05603

PCT Pub. Date: Feb. 23, 1995

[30] Foreign Application Priority Data

Aug. 18, 1993 [GB] United Kingdom .................... 9317199

[51] Int. Cl.$^6$ .......................... G01N 33/12; G01N 33/68; G01N 33/53

[52] U.S. Cl. ................................ 436/21; 436/8; 436/17; 436/18; 436/20; 436/543; 436/825; 436/177; 436/7.1; 436/7.92; 436/7.93; 436/7.94; 436/7.95

[58] Field of Search ..................................... 436/177, 825, 436/8, 19, 18, 20, 21, 17, 543; 435/7.1, 7.92–7.95

[56] References Cited

PUBLICATIONS

England et al (1990) Methods in Enzymology. vol. 158, 157–166.

*Primary Examiner*—Anthony C. Caputa
*Assistant Examiner*—Khalid Masood
*Attorney, Agent, or Firm*—Nixon & Vanderhye P.C.

[57] ABSTRACT

Disclosed is a method for pretreating heat stable proteins derived from a rendered animal material prior to performing an assay for their presence comprising (a) preparing a protein containing extract of the material, (b) removing substantially all or part of the gelatin from the extract and (c) concentrating the remaining protein such that it tests positive for protein by immunoassay at a dilution of greater than 1 in 6,000.

13 Claims, 4 Drawing Sheets

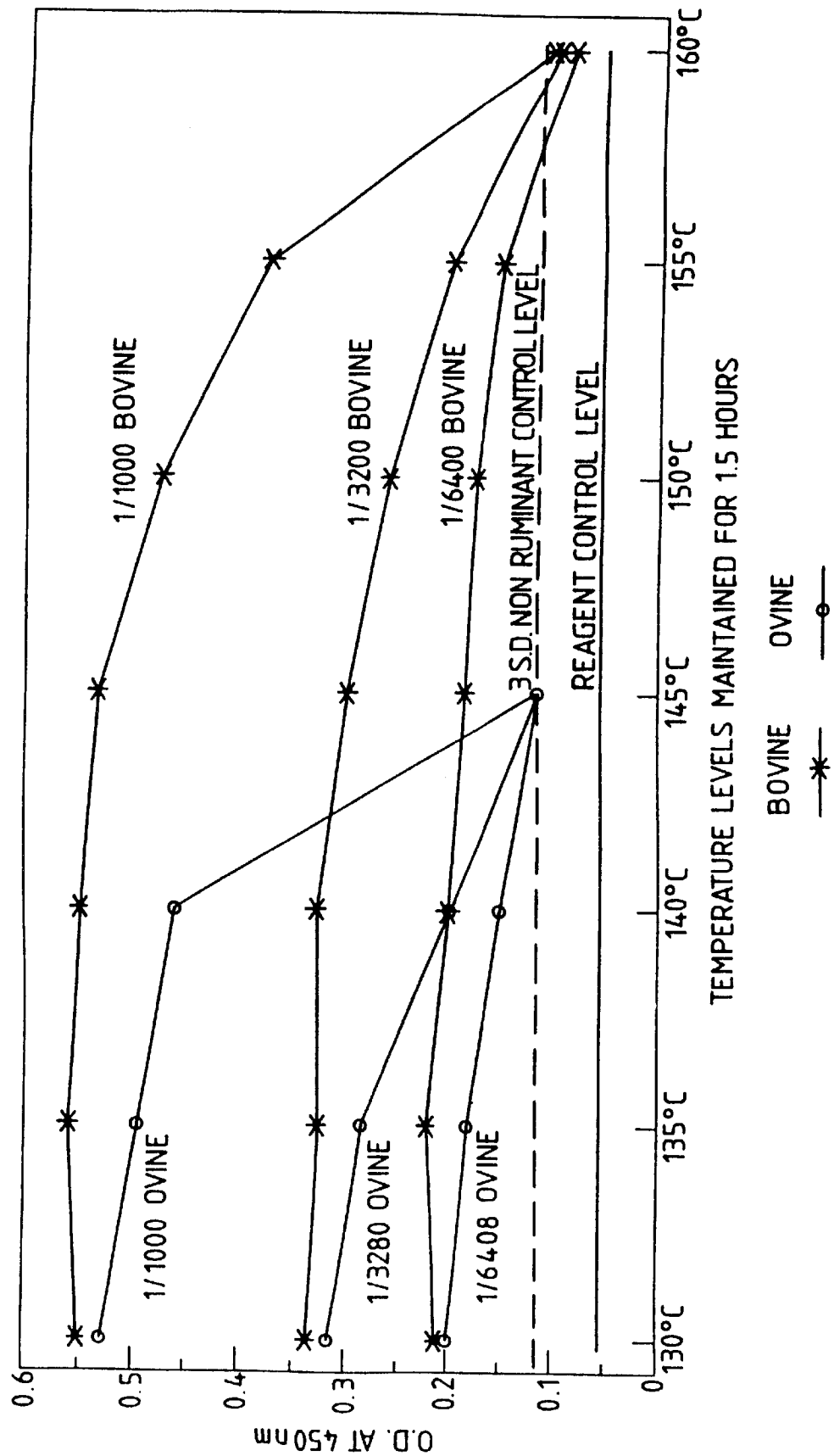

DETECTION OF HEAT STABLE PROTEINS FROM MEAT OF RUMINANT

This application is a 371 of PCT/GB94/01715 filed Aug. 4, 1994.

The present invention relates to a method for the detection of proteins in rendered animal material, and particularly a method for detecting heat stable ruminant proteins in such material.

A ban on rendered ruminant protein in ruminant feedstuffs was instituted by the United Kingdom Ministry of Agriculture, Fisheries and Food in July 1988 in response to outbreak of Bovine Spongiform Encephalopathy—the Bovine Spongiform Encephalopathy Order 1988 (Statutory Instrument 1988/1039). This, and the serious nature of this disease, provides a need to detect these proteins in feedstuffs.

Animal material that passes through a rendering process is subjected to temperatures ranging from 102° C. to 145° C. with a typical exposure time of up to two hours. Current immunological tests aimed at determining the species of origin of resulting meat and bonemeal have limited capability, with little or no sensitivity at below 1% contamination when speciating material cooked above 130° C. for more than one and a half hours; these temperatures being confirmed by differential scanning calorimetry.

Meat speciation is commonly carried out using ELISA systems based on antibodies against muscle heat stable proteins. Berger et al, (1988) J. Association of Official Analytical Chemists, 7, (2), 406–409, have used antisera raised to raw skeletal muscle to detect pork and chicken heated to 120° C. for 15 minutes, while Kang'ethe and Gathuma (1987) Meat Science 19, 265–270, used antisera against cooked muscle proteins, mainly from ruminants, with similar effect. Heat stable proteins have also been demonstrated as present in adrenal glands, brain, testes, heart and kidney.

Material for rendering is composed mainly of bone, fat and viscera, with skeletal muscle being a lesser component. Collagen, which is present in all tissues, converts to a soluble form when heated to become the main constituent of gelatin. Water soluble extracts of meat and bonemeal frequently solidify due to the high gelatin content and this gelatin is capable of depressing the immunoassay sensitivity (e.g. see results in Kang'ethe and Linqvist (1987) in Journal of Science of Food & Agriculture, 39, 179–184.

Thus the immunoassay of heat stable protein in rendered materials such as meat and bonemeal is problematical. Commercial kits currently available can detect bovine and ovine species in these materials at a dilution no greater than one part in 100, and this level of sensitivity decreases in materials that have been treated under high temperature rendering conditions, ie. at about 135° C.–155° C. for up to one and a half hours.

The heat stable sample preparation regimes of Berger et al and Kang'ethe and others can be summarised as follows:

(i) The method of Berger et al (1988) mixes cooked or canned meat with distilled water over a short periods e.g. 1 minutes leaves the mixture to stand for about one hour at room temperature then centrifuges it, the supernatant being used for the assay step.

(ii) The method of Kang'ethe et al (1986) Journal of Science of Food & Agriculture, 37, 157–164 homogenises the meat products in saline in a ratio of about 1:1 (w/v) and then sonicates the mixture at 300 W for 10 minutes, the sonicate is centrifuged at about 2000 g for 15 minutes and resultant supernatant dialysed against saline for 3 days before use in the assay step.

(iii) The method of Kang'ethe and Lindqvist (1987) is initially similar to that of Kang'ethe et al (1986) but uses fresh meat, and after the centrifugation step the supernatant is filtered, centrifuged at 86000×g for 30 minutes, and the resulting supernatant autoclaved at 121° C. for 30 minutes. The autoclaved material is again centrifuged at 2000 g for 15 minutes and the antigens precipitated from the supernatant by addition of 3 vols absolute ethanol; the mixture being left overnight and the precipitate being recovered by centrifugation. The precipitate is then dissolved in saline, concentrated by ultrafiltration (30 kDa cut-off) and fractionated by gel filtration (Sephadex G-200 or G-75). Fractions containing antigen are concentrated by ultrafiltration for assay.

The present inventor has now provided a method for concentrating heat stable proteins in such materials, thus increasing the sensitivity of tests such as the aforesaid immunoassays when they incorporate such preparative method as a preliminary step. This method is surprisingly capable of detecting low concentrations of heat stable proteins in ovine muscle and tissue that has been heated to 145° C., and bovine muscle and tissue that has been heated to 155° C., for periods of 90 minutes such as are found in commercial rendering process.

In a first aspect the present invention provides a method for pretreating heat stable proteins derived from a rendered animal material prior to performing an assay for their presence comprising (a) preparing a protein containing extract of the material, (b) removing substantially all or part of the gelatin from the extract and (c) concentrating the remaining protein, preferably such that it tests positive for protein by immunoassay at a dilution of 1 in 6,000 for rendered meat and bonemeal and 1 in 400 for compound feeds. The present method particularly comprises preparing a liquid buffered extract of the rendered material, removing solid material, e.g. by filtering, adding a salt to the extract at such a concentration as to cause preferential precipitation of gelatin, preferably together with other non-specific proteins and oils, e.g. of plant origin, separating this gelatin precipitate from the extract, increasing the concentration of the salt until a substantial portion of the remainder of the protein is precipitated, and isolating that protein.

Preferred salts are ammonium salts, particularly ammonium sulphate, but other suitable salts will occur to those skilled in the art. Using ammonium sulphate the preferential precipitation of gelatin is conveniently carried out by adding sufficient of the salt to the buffered extract to provide between 30 and 70%, preferably between 30 and 40%, weight salt solution. In order to precipitate the heat stable proteins once the gelatin has been removed further ammonium sulphate is added to give a final concentration in excess of 80% weight, more preferably over 90%, and preferably about 92.5% weight.

The steps of gelatin and heat stable protein removal are conveniently carried out using centrifugation. Most preferably the extract and salt mix is left to stand for a period of hours, e.g. 6 to 18 hours, preferably 12 hours, before centrifugation, preferably standing at a temperature form 25 to 35° C., most preferably about 30° C. After this period the extract salt mix is centrifuged at between 8000 and 10000 g, preferably about 9000 g, and then is preferably filtered to remove cloudy precipitate.

Filtration is conveniently carried out using a micropore filter, e.g. of about 1μ, e.g. a 0.6μ filter. The heat stable proteins which remain in the extract supernatant are isolated preferably by addition of still more salt with constant mixing until they precipitate. With ammonium sulphate this is typically found to occur when the salt saturation is 92.5% and the temperature is maintained at about 30° C. as before. Preferably the mix is shaken to ensure that the salt dissolves and the resultant protein precipitate is separated out by centrifugation under conditions used to isolate the gelatin, plant proteins and oils. Once the heat stable proteins have been precipitated in this way and washed they are conveniently resuspended for the immunoassay or other test methods, whereby the concentration effected is some 30 fold that of the original, with the added advantage that immunological blocking caused by gelatin is avoided.

The buffer used to prepare the initial mix of meat and bonemeal is conveniently such that neutral pH is provided, e.g. pH7.2, and the mixture is preferably blended using an homogenizer and filtered.

In a further aspect the present invention provides a method for assaying a rendered animal material for presence, identity and/or amount of heat stable proteins comprising the pretreatment method as described in the first aspect of the invention, followed by performance of an immunoassay directed at one or more of the proteins and relating the presence, identity and/or concentration of such proteins in the extract to their presences identity and/or concentration in the rendered animal material. Preferred immunoassays use a binding assays e.g. an ELISA or RIA, directed at a number of such proteins such that rapid screening for presence of a number of sources is possible in one assay.

In a still further assay of the present invention there is provided a test kit for assaying the presence, identity and/or amount of a heat stable protein present in or derived from a rendered animal material, comprising a salt, in solid or liquid form, suitable for adding to a extract made from a rendered animal material such that gelatin present therein will be selectively precipitated while leaving substantially all the heat stable protein in solution; together with one or more specific binding agents necessary for carrying out an immunoassay for detecting the presence, identity or concentration of extract protein.

The kit may omit the salt if preferred assay items are included. Typical binding reagents will be specific antibodies raised to heat stable proteins of interest, or to numbers of such proteins. Polyclonal or monoclonal antibodies, or mixtures of these may be used. Capture assay components, such as immobilised antibodies of a first specificity together with solutions of free antibodies to a subset of the first specificity, may be provided. In preferred assays the protein fraction prepared by the method of the invention is resuspended in 2% ovalbumin solution; the antibodies are preferably raised heterologously to both fresh and cooked meat and tissue and PVP is incorporated into the plate washing solution.

The method of the present invention will now be exemplified by way of illustration only by reference to the Figures and Examples. Other embodiments falling into the scope of the claims will occur to those skilled in the art in the light of this and the description above.

FIGURES

FIG. 1: shows a graph of protein concentration of supernatant in mg/100 ml against percentage ammonium sulphate saturation for solutions containing 0.5, 1.0, 1.5 and 2.0% gelatin and indicates the consistency of the supernatant so produced.

Figure 2:
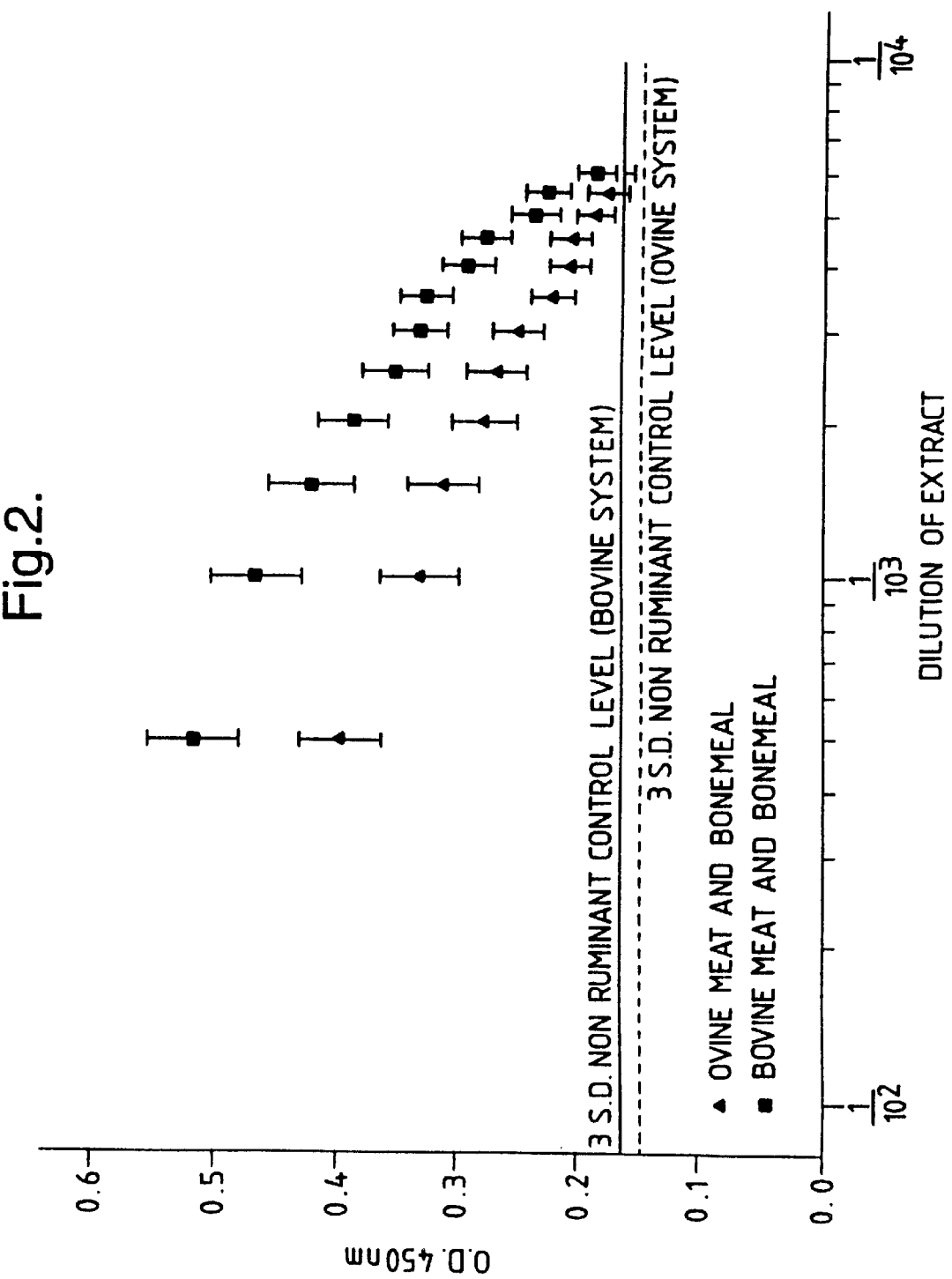

FIG. 2: shows a graph of Optical Density against dilution of extract obtained using the assay of the example for ovine and bovine meat and bonemeals when added to avian/porcine meat and bonemeal.

FIG. 3: shows a graph of the effect of temperature on bovine and ovine tissues at 3 dilutions; 1/1000, 1/3200 and 1/6400; temperatures being maintained for 1.5 hours.

Figure 4A:
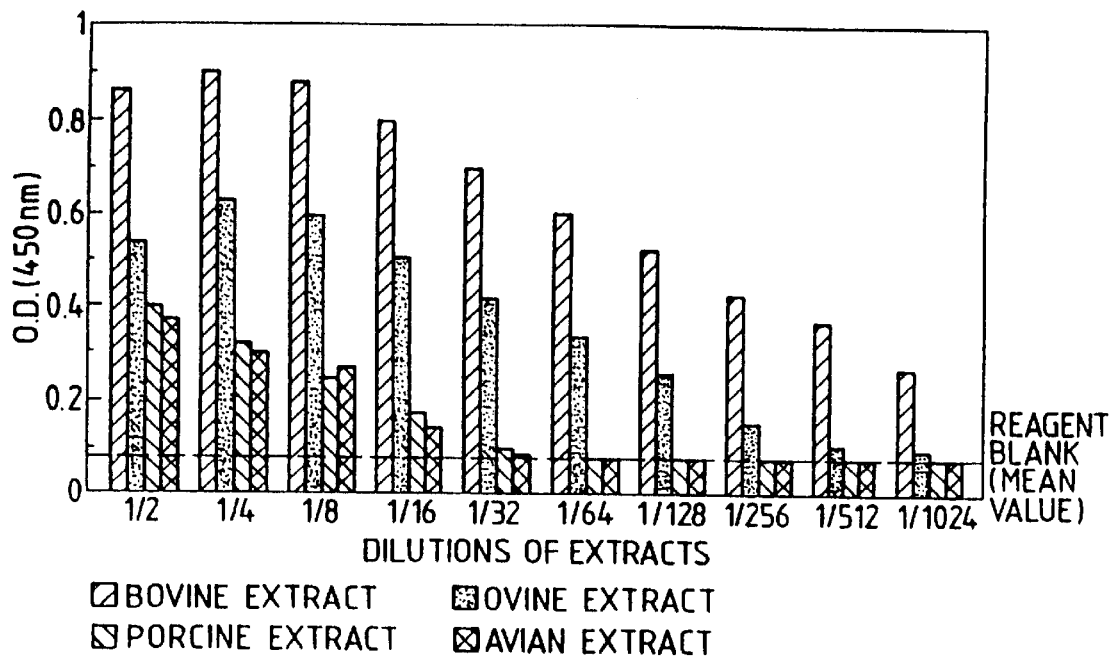

FIG. 4a: shows a histogram of OD at 450 nm against dilution of extracts without blocking agents being present using the assay of the example.

Figure 4B:
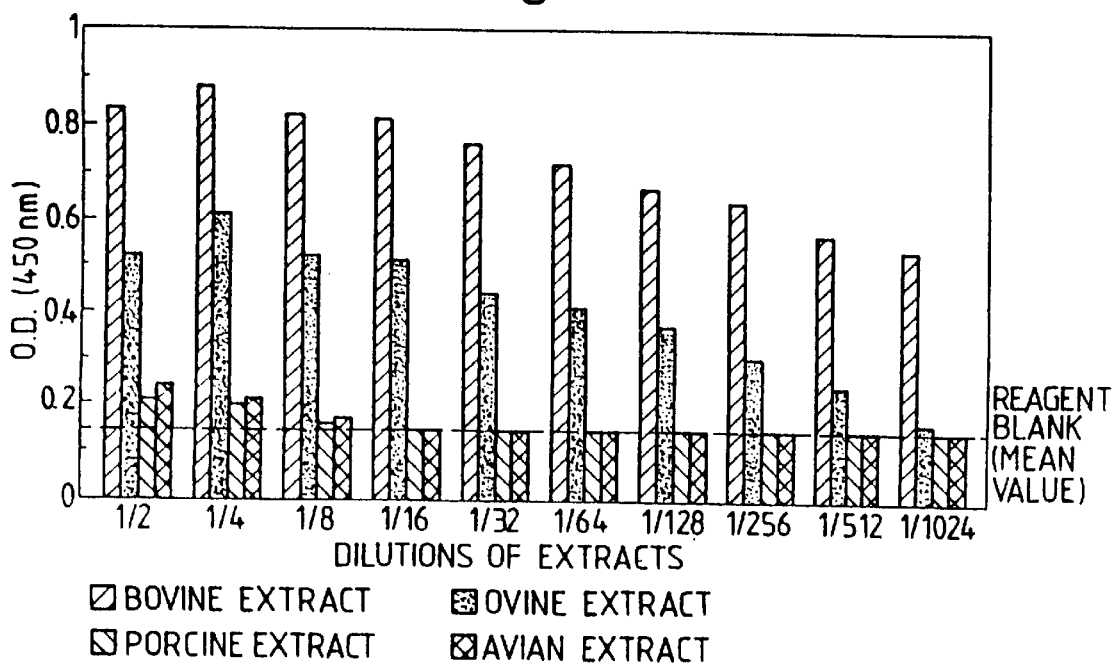

FIG. 4b: shows a histogram of OD at 450 nm against dilution of extracts with PVP and ovalbumin blocking agents present using the assay of the example.

EXAMPLE

Preparation of antibodies to heat stable proteins for use in method:

Four groups of antigens were produced from each of bovine, ovine and porcine material and two groups from poultry (chicken/turkey mixture)-see Table 1. The bovine and ovine antigens were used as immunogens and all antigens were used at a later stage to assess antibody sensitivity and specificity.

TABLE 1

| Bovine, ovine, porcine and avian antigen groups | | | | |
|---|---|---|---|---|
| ANTIGEN MATERIAL | BOVINE | OVINE | PORCINE | AVIAN |
| i Fresh skeletal muscle | + | + | + | + |
| ii Fresh tissue cocktail | + | + | + | − |
| iii Cooked skeletal muscle | + | + | + | + |
| iv Cooked tissue cocktail | + | + | + | − |

Bovine and ovine materials were used as immunogens; + indicates used for antigen production; − indicates not used for antigen production.

Fresh muscle antigen: to avoid possible variations due to breed, age and sex, 50×60 g of lean skeletal muscle samples were taken at random from local abattoirs. 20 g was removed from each sample, pooled and the resultant 1 kg minced and divided into four aliquots of 250 g each. Based upon the method of Berger et al (1988), each aliquot was treated separately to remove non-essential material and the resulting 4 harvests pooled. An XK50/20 column (Pharmacia) was packed with S Sepharose (TM) Fast Flow Cation resin (Pharmacia) and equilibrated with 0.01 M sodium acetate starting buffer pH3.7. The system was linked to an automatic gradient system (Pharmacia) and the pooled extract eluted with a linear gradient composed of 180 ml starting buffer and 167 ml of 0.1 M sodium acetate limit buffer at 20 ml/hour. 3 ml fractions were collected and the eluant constantly monitored at 280 nm absorbance; excess limit buffer was added to ensure complete elution of the major peak after the gradient had run out. The fractions containing the major peak were dialysed against 30% polyethyleneglycol (PEG 20,000 Daltons) to approximately 2 mg protein/ml determined by the Sigma micro determination method.

The total antigen yield was recorded and the isoelectric point (pI) of each of the main proteins was determined by isoelectric focusing using the Phast System (TM, Pharmacia UK Ltd).

Fresh tissue antigen: Heart, adrenals, brain, liver, spleen, kidney, lung and testes were taken from 50 randomly selected carcases to overcome variations as described for collection of skeletal muscle. Tissues associated with alimentary tract were deliberately avoided because of the possible presence of ingested plant or animal proteins. Approximately 20 g of material free from connective tissue and fat were removed from each tissue and the resulting portions pooled and minced. 1 Kg of the pooled cocktail was then used for antigen production and treated as for fresh muscle with total antigen yield and pI band locations recorded.

Cooked skeletal muscle: From each of the original 50×60 g samples of lean skeletal muscle a further 20 g was taken and finely minced. Partially purified thermostable muscle antigen was produced by applying the method of Kang'ethe and Gathuma (1987) Meat Science 19, 265–270. Antigen yield and the main pI positions were recorded.

Cooked tissue antigen: A further 1 Kg of the cocktail of fresh tissues was minced and used for cooked procedure. The method of Kang'ethe and Gathuma was again applied as per the cooked skeletal muscle. Antigen yield and the main pI positions were recorded.

Antisera production: Fifteen sandy lop eared rabbits of approximately 3 Kg each were immunised using the same inoculation procedure as for both "fresh" and "cooked" immunogens. Prevention of ulceration from the primary injection was achieved using a non-ulcerative Freund's complete adjuvant (Morris). 0.05 ml of reconstituted BCG vaccine (Glaxo, Intradermal) was added to the aqueous phase for each 2 ml of oily adjuvant. Rabbits were inoculated subcutaneously at multiple sites on their backs with 1 mg of the aqueous immunogen in an equal volume of the complete adjuvant. Booster injections were given subcutaneously at multiple sites at 4-week intervals (Hardlow and Lane (1988) Laboratory Manual CSH p114–116, using 1 mg of the aqueous immunogen in 2 volumes of oily adjuvant. This continued until a high level of antibody production was obtained; antibody titre to the homologous immunogen was checked prior to and during the inoculation procedure using Ouchterlony's microtechnique double diffusion test of Crowle (1973) Immuno Diffusion, 2nd ed. pg 286–294; Academic Press, N.Y. Rabbits were exsanguinated when a satisfactory titre was achieved and isolation of antibody (IgG/IgA) was carried out by the method of Axelsen et al (1973). The major protein fractions, detected using the Sigma micro-detection method for total protein, pooled and dialysed against 0.1 M phosphate buffered saline, pH7.0. The protein content was again measured and then the pooled fractions split into 1 ml aliquots and stored at −70° C.

Preparation of meat and bone meal sample extracts and test controls:

Each meat and bonemeal used contained a single species (bovine, ovine, porcine and avian) and was produced by a commercial rendering process at 130° C. Each was subjected, in the laboratory, to additional heating to 130° C. for 30 minutes, cooled and stored at −20° C. in 40 g amounts. Extracts of protein for immunoassay were made up by applying either the methods of Berger et al (1988), Kang'ethe and Linqvist (1987), Kang'ethe et al (1986) with the method of the present invention involving removal of gelatin and concentration.

EXAMPLE 1

Pretreatment Step of the Invention

Meat and bonemeal (10 g) and 0.1 M phosphate buffer pH7.2 (90 ml) were mixed, allowed to stand at room temperature for 15 minutes, homogenised in a blender (Waring) at 22° C. for 2 minutes, before being filtered through 4 layers of muslin and then centrifuged at 8890×g for 30 minutes at 22° C. 20 ml aliquots of filtrate were collected and those not immediately required stored at −70° C.

A 35% concentration of anhydrous ammonium sulphate was used to precipitate the gelatins as predetermined using 0.5%, 1.0%, 1.5% and 2% solutions of purified animal gelatins. To achieve this 4.18 g of anhydrous ammonium sulphate was slowly added with constant mixing to each aliquot and the mixture allowed to stand for 12 hours at 30° C., centrifuged at 8890 g for 30 minutes, and any cloudiness removed by filtering through a 0.6μ filter (Millipore Limited, Watford, UK). Remaining protein was concentrated by addition of 8.68 g of anhydrous ammonium sulphate with constant mixing to bring the total ammonium sulphate saturation to 92.5%. The mixture was kept at 30° C. for 12 hours with periodic shaking to ensure all the ammonium sulphate dissolved and the resultant precipitate was separated out by centrifugation at 8890×g at 22° C. for 30 minutes with the supernatant being discarded.

To prevent ammonium sulphate affecting the immunoassay any crystals remaining were immediately redissolved by the careful addition of 20 ml of deionised water and immediately removed by inversion of the tube. The washing was repeated once and the centrifuge tube inverted onto absorbent paper and allowed to drain for 30 minutes. The washing process, if carried out carefully and quickly, has minimal effect on the protein precipitate, but removes all traces of the salt. The precipitate was initially dissolved in 5 drops of 2% Ovalbumin in 0.01 M phosphate buffered saline and the resulting concentrated protein solution diluted 1/5 in 2% Ovalbumin for immunoassay.

EXAMPLE 2

Assay of Materials Provided by Control Methods and Method of the Invention

Test controls: To ensure that a standard approach was applied to all tests a 10 kg pool containing skeletal muscle and selected tissues for each of bovine and ovine species were produced. Each was heated to 130° C. for 60 minutes and the resulting fluid decanted, cooled and passed through muslin to remove fat; further debris was removed by centrifugation and the cleared supernatant retained. The processes of gelatin extraction and protein concentration were applied to the supernatant to produce protein pellets which were then stored at −70° C. and diluted as required for use.

Immunoassay: Two techniques were used: the microtechnique of Ouchterlony's double diffusion test, (Crowle (1973) Immunodifusion, 2nd Edit, Academic Press, New York 286–294) was used for simple screening of antisera and to evaluate the protein extraction methods. Indirect ELISA using horseradish peroxidase was used to allow amplification of sensitivity and specificity to ruminant proteins, subject to the suitability of the antisera.

Double Sandwich ELISA: Antibody conjugation: 20 mg of horseradish peroxidase (Merck Ltd) was activated with 1.0 ml of 0.1 M sodium periodate (Merck Ltd) and any unreacted reagent removed by gel filtration using Sephadex G25 (Pharmacia). Activated peroxidase (HRPX) was conjugated with ruminant antibody after the method of Henning and Nielsen (1987).

Plate coating: 50 μl of antibody were treated with 50 μl of glycine buffer and diluted to a predetermined titre with Tris buffer as described by Jackman (1992) Food Safety and Quality Assurance, application of immunoassay systems; M R A Morgan (Ed), Elsevier Applied Science 215–226. 200 μl aliquots of this were then pipetted into microtitre wells. Each prepared plate was sealed and stood overnight at 4° C. Non specific binding was prevented by washing plates with 0.01 M phosphate buffered saline pH 7.2 containing 0.5% sucrose. 0.1% polyvinylpyrrolidone (PVP) and 0.05% Tween 20. After tapping dry plates were dried at 37° C. for 16 to 24 hours sealed and stored if required at −70° C. for up to 3 months.

ELISA procedure: Optimal dilutions of coating antibody and HRPX conjugated antibody were determined by chequerboard titration against control extracts. Protein extracts were obtained from positive test control material as described and from avian and porcine meat and bonemeal, used as negative controls, using the selection extraction method. All protein extracts were diluted as required using 2% ovalbumin which was also used as the reagent blank. 200 µl controls and reagent blank were added to duplicate wells of flat bottomed microtitre plate strips which had been precoated with coating antibody as previously described. The strips were sealed and incubated at 24° C. for 30 minutes then washed in 0.05% Tween 20 in 0.1 M phosphate buffered saline solution pH7.2. 200 µl of diluted HRPX antibody conjugate was added to each well, the strips sealed and incubated at 24° C. for 30 minutes, the strips washed as before and then 200 µl freshly prepared substrate, produced by mixing equal quantities of Chromagen E8073 and substrate buffer E8071 (Cambridge Veterinary Science) added to each well before shaking at 400 rpm for 6 minutes at 24° C. The reaction was stopped by the addition of 50 µl of 1.8 M sulphuric acid to each well; the absorbence value of each well being measured at 450 nm using an automatic microtitre plate reader.

Evaluation of sera: All 15 sera were tested as both HRPX conjugates and primary plate coating antisera giving a total of 225 test combinations. Each serum was used at a predetermined titre of 1/2000. For each HRPX conjugate/plate coating combination bovine and ovine controls at 1/200, avine and porcine meat and bonemeal extracts at 1/5 and reagent blank (2% ovalbumin in 0.1 M phosphate buffer) were tested. To permit an overall comparison of results between each HRPX conjugate/plate coating combination a target optical density (OD) was set for the control readings and all other results extrapolated to meet the target OD. From these results the HRPX conjugate/plate coating combinations for further development were selected using the following criteria: (i) low OD to avian/porcine meat and bonemeal extracts and the non-selected control; (ii) high ruminant detection titre and (iii) a low reagent background reading. Three standard deviations above the mean reading of the non-ruminant controls was allowed to offset the effect of any non-specific background reading.

Results: Production of Antibody: The yield of antigen extracted from 1 kg amounts of fresh muscle or tissue using a modification of the method of Berger et al (1988) J. Association of Official Analytical Chemists 7(2), 406–409 was considerably less than that obtained from the cooked muscle tissue by the method of Kang'ethe and Gathuma (1987) Meat Science, 19,265–270. The yields, determined by protein assay using the Sigma Micro-determination method, are shown in Table 2.

TABLE 2

| | Extraction method for antigen | |
|---|---|---|
| MATERIAL | Berger et al | Kang'ethe & Gathuma |
| Bovine muscle | 54.76 | 276.52 |
| Bovine tissue | 50.11 | 234.52 |
| Ovine tissue | 39.07 | 195.73 |
| Ovine tissue | 136.54 | 442.13 |
| Porcine muscle | 52.92 | 198.78 |
| Porcine tissue | 129.00 | 301.10 |
| Avian muscle | 40.79 | 224.14 |

When subject to isloelectric focusing using the Phast System at a pH gradient of 3.5–9.5 (Pharmacia UK Ltd) the main pI bands from the fresh muscle and tissue were found as follows: Identical pI bands were evident at pH5.15 for bovine muscle and porcine tissue, pH5.5 for bovine tissue and ovine tissue and pH8.6 for bovine muscle and porcine muscle. No major bands were found in the antigens extracted from cooked muscle or tissue.

Antisera production: Antisera specificity are given in Table 3 below.

TABLE 3

| | | Ouchterlony's microtechnique double diffusion test results | | | | | | | | | | | | | |
|---|---|---|---|---|---|---|---|---|---|---|---|---|---|---|---|
| Rabbit | | Antigens (Fresh) Berger et al | | | | | | | Antigens (Cooked) Kang'ethe & Gathuma | | | | | | |
| No. | Antiserum | BM | BT | OM | OT | PM | PT | AM | BM | BT | OM | OT | PM | PT | AM |
| 1 | Bovine muscle (F) | 3+ | 4+ | − | − | − | − | − | 4+ | 4+ | − | − | − | − | − |
| 2 | | 3+ | 4+ | + | − | − | + | − | 4+ | 4+ | − | − | − | − | − |
| 25 | | + | 2+ | 4+ | 4+ | + | 2+ | − | + | 2+ | 2+ | 2+ | − | − | − |
| 9 | Bovine tissue (F) | 3+ | 4+ | − | + | − | − | − | 3+ | 2+ | + | − | − | − | − |
| 10 | | 4+ | 4+ | + | + | − | + | − | 3+ | 4+ | + | − | − | − | − |
| 3 | Ovine muscle (F) | + | + | 4+ | 2+ | − | + | − | − | + | + | 2+ | − | − | − |
| 4 | | + | + | 3+ | 2+ | − | − | − | − | + | 2+ | 2+ | − | − | − |
| 11 | Ovine tissue (F) | 4+ | 4+ | + | + | − | − | − | 4+ | 4+ | − | − | − | − | − |
| 13 | Bovine muscle (C) | + | 2+ | − | + | − | − | − | 3+ | 3+ | − | − | − | − | − |
| 14 | | 4+ | 4+ | + | + | − | − | − | 3+ | 4+ | − | − | − | − | − |
| 19 | Bovine tissue (C) | + | + | + | + | − | − | − | 3+ | 3+ | − | + | − | − | − |
| 22 | | + | 2+ | + | 2+ | − | − | − | 4+ | 3+ | − | 2+ | − | − | − |
| 15 | Ovine muscle (C) | − | 31 | 2+ | 2+ | − | − | − | + | − | 3+ | 3+ | − | − | − |
| 16 | | + | + | 2+ | 2+ | − | − | − | 2+ | + | 3+ | 3+ | − | − | − |

TABLE 3-continued

Ouchterlony's microtechnique double diffusion test results

| Rabbit | | Antigens (Fresh) Berger et al | | | | | | | Antigens (Cooked) Kang'ethe & Gathuma | | | | | | |
|---|---|---|---|---|---|---|---|---|---|---|---|---|---|---|---|
| No. | Antiserum | BM | BT | OM | OT | PM | PT | AM | BM | BT | OM | OT | PM | PT | AM |
| 23 | Ovine tissue (C) | 2+ | + | 2+ | 4+ | + | + | − | + | 3+ | 3+ | 4+ | − | + | − |

+ weak 2+ moderate 3+ strong 4+ very strong − negative
B bovine O ovine P porcine A avian M muscle T tissue F fresh C cooked The majority of these antisera show a degree of cross-reactivity between bovine and ovine species antigens, with 5 out of 15 showing some response to porcine antigen.

The consistency and protein content of comparative gelatin solutions at 4° C. following ammonium sulphate precipitation is shown in FIG. 1, while Table 4 demonstrates the effect of gelatin removal on the protein content of bovine and ovine meat and bonemeal.

TABLE 4

Protein content of bovine and ovine meat and bonemeal extract:

| | Bovine | Ovine |
|---|---|---|
| Total Protein | 182 mg/ml | 300 mg/ml |
| After gelatin and associated protein precipitation | 5.38 mg/ml (2.95%) | 2.3 mg/ml (0.77%) |
| Gelatin-free proteins available in 1/6000 dilution of a sample | 0.8966 μg/ml | 0.3833 μg/ml |

Extraction methods:

The choice of extraction method was made by assessing the three methods Berger et al (1988), Kang'ethe et al (1986) and Kang'ethe and Linqvist (1987); results being set out below in Table 5.

Evaluation of antisera:

Antisera were initially assessed against bovine and ovine meat and bonemeal extracts and the cross-reactivity found is set out in Table 6 below.

TABLE 5

Comparison of protein extraction methods expressed as maximum detectable protein dilution tested against pooled bovine ovine antisera using Ouchterlony's microtechnique double diffusion test.

| | Bovine extract dilution | | | | | | | Ovine extract dilution | | | | | | |
|---|---|---|---|---|---|---|---|---|---|---|---|---|---|---|
| Method | 0 | 2 | 4 | 8 | 16 | 32 | 64 | 0 | 2 | 4 | 8 | 16 | 32 | 64 |
| Gelatin removal +protein conc | + | + | + | + | + | + | − | + | + | + | + | + | − | − |
| Berger (1988) | − | − | − | − | − | − | − | − | − | − | − | − | − | − |
| Kangethe (1986) | + | − | − | − | − | − | − | − | − | − | − | − | − | − |
| Kangethe (1987) | + | + | − | − | − | − | − | − | − | − | − | − | − | − |

TABLE 6

Detectable levels of antigen from gelatin free meat and bonemeal extracts tested against each antigen using Ouchterlony's microtechnique double diffusion test

| Rabbit | Antiserum expressed | Maximum detectable dilution of meat and bonemeal protein extracts | | | |
|---|---|---|---|---|---|
| No. | as immunogens used | B | O | P | A |
| 1 | B.M-F | 1/32 | 1/16 | 0 | 0 |
| 2 | " | 1/64 | 1/2 | Neat | 0 |
| 25 | " | 1/4 | 1/32 | 0 | 0 |
| 9 | B.T-F | 1/32 | 1/16 | 0 | 0 |
| 10 | " | 1/32 | 1/16 | 0 | 0 |
| 3 | O.M-F | 1/16 | 1/16 | 0 | 0 |
| 4 | " | 1/16 | 1/32 | Neat | 0 |
| 11 | O.T-F | 1/64 | 1/16 | 0 | 0 |
| 13 | B.M-C | 1/16 | 0 | 0 | 0 |
| 14 | " | 1/16 | 0 | 0 | 0 |
| 19 | B.T-C | 1/32 | 1/8 | 0 | 0 |
| 22 | " | 1/16 | 1/16 | 0 | 0 |
| 15 | O.M-C | 1/4 | 1/8 | 0 | 0 |
| 16 | " | 1/4 | 1/16 | 0 | 0 |
| 23 | O.T-C | 1/16 | 1/32 | 0 | 0 |

Indirect ELISA:

Direct comparison of the extrapolated results from the 225HRPX conjugate/plates coating antisera combinations revealed 38 giving acceptably high optical density (OD) readings to the bovine or ovine controls at 450 nm. Sixteen out of the 38 combinations of antisera/HRPX conjugates were selected on the basis of the 3 chosen criteria; these being low OD of ≦0.08 for avian/porcine meat and bonemeal, high ruminant detection titre of >1/2000 and a low reagent background OD reading of ≦0.08.

Chequerboard titration: The optimum titre of sera of each of the selected HRPX conjugate/plate coating antisera combinations was determined by running dilutions of both HRPX conjugate and plate coating antisera against a fixed dilution of homologous control and meat and bonemeal extracts to produce the final assay protocol. It was found that the bovine and ovine systems could be separated on the basis of the chequerboard results.

Test evaluation:

Initially 50×20 g dry meat and bonemeal samples were tested double blind. Bovine, ovine, porcine and avian meat and bonemeals were mixed in varying proportions to simulate a range of ruminant contamination. A representative sample could not be achieved below 1 part in 400 for a 20 g dry mix because of the varied particulate composition of the meat and bonemeal; this was therefore a limiting factor for the dry mix test. Ten avian meat and bonemeal samples at a dilution of 1 part in 5 were used as the non-ruminant controls and 3 standard deviations above the mean value chosen as the non-ruminant limit. All 50 test samples were correctly identified as ruminant or non-ruminant.

Results are shown in Table 7.

Sensitivity:

To evaluate the sensitivity of the test, liquid extracts of avian and porcine meat and bonemeals were contaminated with decreasing amounts of liquid extracts of bovine and ovine meat and bonemeals. Both bovine and ovine extracts were detectable up to the extinction dilution of 1/6400, but dilutions greater than this gave an optical density below the 3 standard deviation non-ruminant control limit.

Results are shown in FIG. 2.

TABLE 7

Double blind results on mixes of meat and bonemeal.

| Sample No. | Mix composition | | | | OD 450 nm above NR control |
|---|---|---|---|---|---|
| | A | P | B | O | |
| 1 | 100 | — | — | — | 0 |
| 2 | — | — | 100 | — | 0.632 |
| 3 | 75 | 25 | — | — | 0 |
| 4 | 50 | 50 | — | — | 0 |
| 5 | — | 95 | — | 5 | 0.338 |
| 6 | 99.5 | — | 0.5 | — | 0.325 |
| 7 | — | 100 | — | — | 0 |
| 8 | — | — | — | 100 | 0.468 |
| 9 | — | — | 5 | 95 | 0.605 |
| 10 | — | 99.75 | 0.25 | — | 0.301 |
| 11 | 99.75 | — | — | 0.25 | 0.251 |
| 12 | 50 | 50 | — | — | 0 |
| 13 | 100 | — | — | — | 0 |
| 14 | — | 100 | — | — | 0 |
| 15 | — | 95 | 5 | — | 0.422 |
| 16 | — | 99.5 | 0.5 | — | 0.343 |
| 17 | 95 | — | — | 5 | 0.336 |
| 18 | 50 | 49.75 | — | 0.25 | 0.233 |
| 19 | — | — | 49.75 | 0.05 | 0.544 |
| 20 | 100 | — | — | — | 0 |
| 21 | 80 | — | 20 | — | 0.404 |
| 22 | — | 90 | 10 | — | 0.363 |
| 23 | — | 99 | — | 1 | 0.290 |
| 24 | — | 99 | — | 1 | 0.198 |
| 25 | — | 90 | 10 | — | 0.353 |
| 26 | — | 100 | — | — | 0 |
| 27 | — | — | — | 100 | 0.535 |
| 28 | — | — | 100 | — | 0.609 |
| 29 | — | — | 10 | 90 | 0.563 |
| 30 | 100 | — | — | — | 0 |
| 31 | 95 | — | 2.5 | 2.5 | 0.386 |
| 32 | 95 | — | — | 5 | 0.365 |
| 33 | 99 | — | 1 | — | 0.201 |
| 34 | — | 99.5 | 0.5 | — | 0.233 |
| 35 | — | 95 | 5 | — | 0.328 |
| 36 | 80 | — | — | 20 | 0.411 |
| 37 | 50 | — | 50 | — | 0.575 |
| 38 | — | — | 50 | 50 | 0.611 |
| 39 | — | 100 | — | — | 0 |
| 40 | 100 | — | — | — | 0 |
| 41 | — | 95 | 5 | — | 0.313 |
| 42 | — | — | 100 | — | 0.577 |
| 43 | 99 | — | 1 | — | 0.316 |
| 44 | — | 99.5 | — | 0.5 | 0.211 |
| 45 | — | 100 | — | — | 0 |
| 46 | — | — | — | 100 | 0.521 |
| 47 | 90 | — | 10 | — | 0.403 |
| 48 | 99.75 | — | — | 0.25 | 0.234 |
| 49 | — | 99.75 | 0.25 | — | 0.301 |
| 50 | 25 | 25 | 25 | 25 | 0.530 |

NR = non-ruminant

Evaluation of effect of temperature: The effect of temperature and time upon the ruminant proteins and the efficacy of the immunoassay were evaluated by heating small pieces of fresh bovine and ovine muscle at increasing tempertures above 130° C. for up to 90 minutes. Extracts taken for each temperature were tested at 3 dilutions, ie. 1/1000, 1/3200 and 1/6400, and the optical density plotted. The bovine muscle was detectable at all three dilutions at 155° C. but none were detectable at 160° C. Ovine muscle detection declined rapidly and was not detectable at temperatures above 145° C. Results are shown in FIG. 3. The sensitivity of the test to cooked ruminant proteins as compared with those produced by rendering, e.g. fish and bonemeal, is substantially higher. The titres of detection therefore address only those of meat and bonemeal and meet the terms of this particular immunoassay.

The results above show that the test method of the present invention makes it possible to detect ruminant heat stable proteins at 0.8966 µg/ml for bovine species and 0.3833 µg/ml for ovine species. Furthermore, the cross-reactivity studies on antibodies show that when raising antisera for use in the test method incorporating the sample preparation method of the invention, these should be raised heterologously to both fresh and cooked antigens, one each as the coating antibody and signal generating antibody. Incorporation of polyvinylpyrrolidone (PVP) into the plate washing solution reduces background readings while further reduction occurs if 2% ovalbumin solution is used to suspend the final concentrated sample. FIGS. 4a and 4b illustrate the effects of these inclusions. Furthermore, for compound feeds it is found that use of the upper part of the range of ammonium sulphate concentration, ie. about 70% by weight, e.g. 68%, is required to remove plant proteins and oils prior to protein concentration.

I claim:

1. A method for pretreating heat stable proteins derived material from a rendered animal prior to performing an assay for their presence comprising the steps of:
   (a) preparing a protein-containing liquid extract from material from a rendered animal,
   (b) adding a salt to the extract to precipitate gelatin from the extract,
   (c) separating the gelatin precipitated from the extract,
   (d) increasing the concentration of the salt until a portion of the remaining protein is precipitated and isolating that protein.

2. A method according to claim 1 wherein in step (d), the remaining proteins are concentrated until it tests positive for proteins by immunoassay at a dilution of 1 in 6,000 proteins extract to aqueous test medium when the proteins are derived from a material obtained from rendered meat and bonemeal and at a dilution of 1 in 400 when the proteins are derived from a material that has been included in feeds.

3. A method according to claim 1 wherein step (a) comprises preparing a liquid buffered extract of the rendered material and removing any solid material therefrom.

4. A method as claimed in claim 1 wherein the salt used is an ammonium salt.

5. A method as claimed in claim 4 wherein the proteins are derived from a material which is of a compound feed and the salt is added to the buffered extract to provide between a 30 and 70% weight salt solution and wherein precipitation of gelatin and plant proteins occurs.

6. A method for pretreating heat stable proteins derived from a rendered animal material which has been incorporated into a compound feed, prior to performing an assay for their presence comprising preparing a liquid buffered extract of the rendered material, removing solid material from the extract, adding an ammonium salt to the extract to provide from 30 to 70% weight salt solution, separating the precipitate from the extract, increasing the concentration of the salt until a portion of the remainder of the proteins are precipitated, and isolating those proteins.

7. A method as claimed in claim 6 wherein the proteins have not been incorporated into a compound feed and sufficient of the salt is added to the buffered extract to provide between a 30 and 40% weight salt solution.

8. A method as claimed in claim 6 wherein, in order to precipitate the heat stable proteins after the first precipitate has been removed, further salt is added to give a final concentration in excess of 70% weight.

9. A method as claimed in claim 8 wherein the salt is ammonium sulphate and is added to produce a final concentration in excess of 90% weight.

10. A method as claimed in claim 1 wherein the ammonium sulphate is added to produce a final concentration of about 92.5% weight.

11. A method as claimed in claim 1 wherein the steps of separating gelatin and isolating heat stable proteins carried out using centrifugation.

12. A method as claimed in claim 1 wherein the rendered animal material is in the form of a mix of meat and bonemeal and the buffer used to prepare the initial mix of meat and bonemeal confers a neutral pH.

13. A method as claimed in claim 1 wherein the extract is prepared by blending the rendered animal material with the buffer using an homogenizer, and then filtering the resultant mixture.

* * * * *